United States Patent [19]

Kolesar, Jr.

[11] Patent Number: 5,071,770

[45] Date of Patent: Dec. 10, 1991

[54] METHOD FOR GASEOUS COMPONENT INDENTIFICATION WITH #3 POLYMERIC FILM

[75] Inventor: Edward S. Kolesar, Jr., Beavercreek, Ohio

[73] Assignee: The United States of America as represented by the Secretary of the Air Force, Washington, D.C.

[21] Appl. No.: 608,852

[22] Filed: Nov. 5, 1990

Related U.S. Application Data

[62] Division of Ser. No. 405,824, Sep. 5, 1989.

[51] Int. Cl.$^5$ .............................. G01N 27/00
[52] U.S. Cl. .................... 436/151; 436/149; 422/83; 422/90; 422/98; 204/406; 324/439
[58] Field of Search .............. 436/151, 149; 422/83, 422/90, 98; 204/406, 400, 424, 431; 324/438, 439, 425

[56] References Cited

U.S. PATENT DOCUMENTS

| | | | |
|---|---|---|---|
| 3,469,184 | 9/1969 | Lambi et al. | 324/65 |
| 3,507,145 | 4/1970 | Lob et al. | 73/23 |
| 3,719,564 | 3/1973 | Lilly, Jr. et al. | 204/1 |
| 3,831,432 | 8/1974 | Cox | 73/23 |
| 3,910,763 | 10/1975 | Poziomek et al. | 23/232 |
| 4,020,830 | 5/1977 | Johnson et al. | 128/2 |
| 4,158,807 | 6/1979 | Senturia | 324/71 |
| 4,180,771 | 12/1979 | Guckel | 324/71 |
| 4,218,298 | 8/1980 | Shimada et al. | 204/195 |
| 4,238,757 | 12/1980 | Schenck | 357/25 |
| 4,322,680 | 3/1982 | Janata et al. | 324/71 |
| 4,368,480 | 1/1983 | Senturia | 357/25 |
| 4,397,714 | 8/1983 | Janata et al. | 204/1 |
| 4,437,969 | 3/1984 | Covington et al. | 204/403 |
| 4,542,640 | 9/1985 | Clifford | 73/23 |
| 4,572,900 | 2/1986 | Wohltjen | 436/151 |
| 4,636,767 | 1/1987 | Barger et al. | 338/34 |
| 4,637,987 | 1/1987 | Minten et al. | 436/151 |
| 4,670,405 | 6/1987 | Stetter et al. | 436/151 |
| 4,725,733 | 2/1988 | Horman et al. | 250/339 |
| 4,744,954 | 5/1988 | Campbell et al. | 436/151 |

OTHER PUBLICATIONS

S. D. Santuria et al., The Charge-flow Transistor: A New MOS Device, *Applied Physics Letter*, vol. 30, No. 2, pp. 106–108, Jan. 15, 1977.

R. L. Smith et al., Transient Phenomena in Ion Sensitive Field Effect Transistors, *Journal of the Electro Chemical Society*, vol. 122, No. 7, p. 1599.

S. L. Garverick, et al., An MOS Chip for Surface Impedance Measurement and Moisture Mon. 26th Int. Electron Div. Meet. Inter. Elect. Devices Meeting, Tech. Digest, vol. 7, paper E6, pp. 685–688, published by the Institute of Electrical and Electronic Engineers, New York, N.Y.

Chemical Selectivity of Field-Effect Transistors, *Sensors and Actuators*, 12, 1987, pp. 121–128, Aug. 26, 1986.

Journal of The Chemical Society, A Journal of Physical Chemistry, Van Ewyk et al., Dec. 1980.

Micro Electronic Circuits, Dedra et al., 1982, HRW Series on Electrical and Computer Engineering.

Semiconductor Devices Physics and Technology S. M. SZE, John Wiley & Sons, 1985.

*Primary Examiner*—Robert J. Warden
*Assistant Examiner*—Laura E. Collins
*Attorney, Agent, or Firm*—Gerald B. Hollins; Donald J. Singer

[57] ABSTRACT

A sensor having an interdigitated gate electrode field effect transistor (IGEFET) coupled to an electron beam evaporated copper phthalocyanine thin film is used to selectively detect parts-per-billion concentration levels of atmosphere contaminants such as nitrogen dioxide ($NO_2$) and diisopropyl methylphosphonate (DIMP). The sensor is excited with a voltage pulse, and its time- and frequency-domain response are examined. The envelopes of the magnitude of the normalized difference frequency spectrums reveal features which unambiguously distinguish the $NO_2$ and DIMP exposures.

16 Claims, 9 Drawing Sheets

METHOD FOR GASEOUS COMPONENT INDENTIFICATION WITH #3 POLYMERIC FILM

RIGHTS OF THE GOVERNMENT

The invention described herein may be manufactured and used by or for the Government of the United States for all governmental purposes without the payment of any royalty.

This is a division of application Ser. No. 07/405,824, filed Sept. 5, 1989.

BACKGROUND OF THE INVENTION

This invention relates to the field of gaseous component presence detection and measurement by way of electrical conductivity changes.

The detection of low-level gaseous contaminants in the atmosphere and in other gaseous environments continues to be an important and evolving chapter in the measurement art. In addition to the expected chemical warfare and defensive or protective apparatus implications of this technology, there exists a need for more convenient and reliable instrumentation for the detection of unintentional or casual pollutant materials in the areas where people live and work. Two important and typical classes of atmospheric pollutants falling within these contaminated environment categories are the organophosphorus compounds used for pest control, chemical warfare, and certain industrial purposes, and the oxides of nitrogen, particularly nitrogen dioxide ($NO_2$), that are unintentionally admitted into the atmosphere from automotive exhaust, combustion stacks, high temperature combustion events and other sources. Nitrogen dioxide is, for example, a known constituent of some ingredient decomposition reactions and, in fact, can be used as a characteristic indicator associated with the progression of these decomposition reactions and ingredient status.

A significant portion of organophosphorus contaminants are found to contain either the phosphoryl or thiophosphoryl group of atoms. Since diisopropyl methylphosphonate (DIMP) is a phosphoryl containing compound having low-toxicity, and significantly documented properties, it is convenient for use as a model organophosphorus gaseous compound in the description of the present invention.

The coated bulk-wave piezoelectric quartz crystal microbalances and surface acoustic wave transducers have recently been considered candidate technologies for detecting and measuring such pollutants as nitrogen dioxide, $NO_2$, and the organophosphorus compounds. These devices have been reported in various publications including the reports of E. P. Scheide and G. G. Guilbault in "Analytical Chemistry", volume 44, pages 1764-1768, 1972; W. M. Shackelford and G. G. Guilbault, in "Analytica Chimica Acta", volume 73, pages 383-389, 1974; Y. Tomita and G. G. Guilbault, in "Analytical Chemistry", volume 52, pages 1484-1489, 1980; G. G. Guilbault, Y. Tomita, and E. S. Kolesar, Jr. in "Sensors and Actuators", volume 2, pages 43-57, 1981; G. G. Guilbault, J. Affolter, and E. S. Kolesar, Jr. in "Analytical Chemistry", volume 53, pages 2057-2060, 1981; K. H. Karmarker and G. G. Guilbault in "Analytica Chimica Acta", volume 75, pages 111-117, 1975; and L. M. Webber, J. Hlavay, and G. G. Guilbault in "Mikrochimica Acta," volume 1, pages 351-358, 1978.

Surface acoustic wave detection devices have similarly been reported by A. W. Barendsz, J. C. Vis, M. S. Nieuwenhuizen, E. Nieuwkoop, M. J. Vellekoop, W. J. Ghijsen, and A. Venema in "Proceedings of the IEEE Ultrasonics Symposium", page 586, 1985; M. S. Nieuwenhuizen, A. W. Barendsz, "Electronic Letters", volume 22, pages 184-185, 1986; A. Venema, E. Nieuwkoop, W. J. Ghijsen, A. W. Barendsz, and M. S. Nieuwenhuizen in "IEEE Transactions on Ultrasonics, Ferroelectrics, and Frequency Control", volume UFFC-34, pages 148-154, 1987; M. S. Nieuwenhuizen and A. W. Barendsz in "Sensors and Actuators", volume 11, pages 45-62, 1987; M. S. Nieuwenhuizen, A. Nederlof, A. W. Barendsz in "Analytical Chemistry", volume 60, pages 230-235, 1988. Detectors based on coated bulk-wave piezoelectric crystal microbalances and surface acoustic wave devices are, however, found to have significant limitations including a notable lack of sensitivity and undesirable response to moisture along with difficulty in reproducing identical measurement results.

The concept of utilizing a chemiresistor or interdigitated electrode electrical resistance structure for monitoring impedance changes caused by a chemical reaction have also been reported in the technical literature by F. W. Kutzler, W. Barger, A. Snow, and H. Wohltjen in "Thin Solid Films", volume 155, page 155, 1987. Similarly, epoxy cure monitoring and the interaction of $NO_2$ and organophosphorus compounds with phthalocyanine films have also been considered as is evidenced by the work of S. Baker, G. G. Roberts, and M. C. Petty in "IEE Proceedings", Part 1, volume 130, pages 260-263, 1983; and by H. Wohltjen, W. Barger, and A. Snow, in "Proceedings of the IEEE International Conference on Solid State Sensors and Actuators", pages 410-413, 1985; by H. Wohltjen, W. Barger, A. Snow, and N. L. Jarvis in "IEEE Transactions on Electron Devices", volume ED-32, pages 1170-1174, 1985; by R. H. Tregold, M. C. J. Young, B. Hodge, and A. Hoorfar in "IEE Proceedings", Part 1, volume 132, pages 151-156, 1985; T. Jones and B. Bott in "Sensors and Actuators", volume 9, pages 27-37, 1986; and P. M. Burr, P. D. Jeffery, J. D. Benjamin, and M. J. Uren in "Thin Solid Films", volume 151, pages L111-L113, 1987.

It is important to note, however, that most of these previous investigations of the chemiresistor and phthalocyanine embodiments, thereof, have focused on the direct current electrical conductivity changes in the chemically active film while only a few investigators have considered the alternating current behavior of these films and, notably, have considered this alternating current behavior only at specific and single alternating current frequencies.

Additional evidence of previous gaseous component identification investigations is also to be found in the patent art including the patent of W. R. Barger et al, U.S. Pat. No. 4,636,767, wherein an interdigitated finger structure and a phthalocyanine film are used in combination with direct current excitation of the detecting cell for the monitoring of gaseous components. Also included in this art is the patent of J. R. Stetter, U.S. Pat. No. 4,670,405, which considers the time response of a plurality of sensor elements taken over time periods measured in tens of seconds and processed in a microprocessor computer.

Also included in the patent art is the detection and measuring system of P. K. Clifford described in U.S. Pat. No. 4,542,640 which includes a plurality of differing semiconductor gas sensor cells and apparatus for measuring their electrical resistance and for processing the resulting signals. In addition, the patent of R. H. Duhlgren et al, U.S. Pat. No. 4,725,733, discloses an optically based detection arrangement for chemical warfare nerve agents, and the patent of E. J. Poziomek et al, U.S. Pat. No. 3,910,763, discloses a chemical reaction based detection arrangement for organophosphorus compounds.

SUMMARY OF THE INVENTION

The present invention concerns a detector that is suitable for identifying gaseous components, such as organophosphorus compounds and nitrogen dioxide in a challenge gas mixture. Identification is accomplished in the detector apparatus by way of the chemical reaction of these components with a thin film chemiresistive detecting element. According to a further aspect of the invention, excitation of the chemiresistive thin film element with a square-wave approximation to the ideal impulse function, herein called simply "an impulse function", is employed along with Fourier analysis of the resistive element's time response. Additional aspects of the invention include multiplex consideration of plural detecting element signals of the described type from an array having a large number of elements, and therefore, an overall unique response pattern for a plurality of challenge gas components.

It is an object of the present invention, therefore, to provide a chemiresistor gas detection apparatus which employs a broad frequency spectrum excitation voltage signal for the chemiresistor element.

It is another object of the invention to provide a chemiresistor detection apparatus that employs an impulse voltage signal as the excitation source for the chemiresistor.

It is another object of the invention to provide a combined impulse voltage signal excitation of a chemiresistive detection element and the corresponding Fourier transform analysis of the chemiresistor's output signal.

It is another object of the invention to provide a chemiresistor detection arrangement especially adapted to the detection of the variety of components in a challenge gas mixture.

It is another object of the invention to provide a chemiresistor detection apparatus that is especially adapted to the detection of organophosphorus compound and nitrogen dioxide related gaseous pollutants.

It is another object of the invention to provide a gaseous pollutant detection arrangement that is based on conductivity variations in a thin film chemiresistive sensing element.

It is another object of the invention to provide a thin film and interdigitated electrode sensing element gaseous detection apparatus employing the benefits of a locally disposed high-input impedance field effect transistor amplifier.

It is another object of the invention to provide a chemiresistor gas detection apparatus which employs a metal-doped phthalocyanine thin film as a sensing element.

It is another object of the invention to provide a gaseous detection apparatus which employs a copper phthalocyanine thin film material as a sensing element.

It is another object of the invention to provide a chemiresistor gaseous detection apparatus that is operative with both a minimal duration of challenge gas exposure and a short period of preconditioning.

It is another object of the present invention to provide an impulse and Fourier transformation embodying chemiresistive detection apparatus having a plurality of differently responding chemiresistive element species capable of a collectively unique response to a plurality of challenge gas components.

It is another object of the invention to provide a chemiresistive detection apparatus employing a plurality of detector element species which may be conveniently integrated into a detection system through the use of a microprocessor and multiplexing technique.

Additional objects and features of the invention will be understood from the following description and the accompanying drawings.

These and other objects of the invention are achieved by an apparatus for monitoring gaseous concentrations in a challenge gas effluent which includes the combination of a gaseous sensor member having an array of first and second interposed electrical conductors and an overlying chemically-reactive polymeric thin film membrane member in electrical contact therewith, the instantaneous electrical impedance between the conductors being determined by the conductivity of the thin film membrane member and means for exposing the thin film membrane member to the challenge gas, and energy sourcing means having a harmonic rich multiple sinusoidal component waveform output signal for energizing the sensor member, and waveform analysis means including Fourier transformation means for determining the spectral distribution of sensor member conductivity variation imposed modifications of the sourcing means signal in response to an unknown effluent exposure.

DETAILED DESCRIPTION

Figure 1:
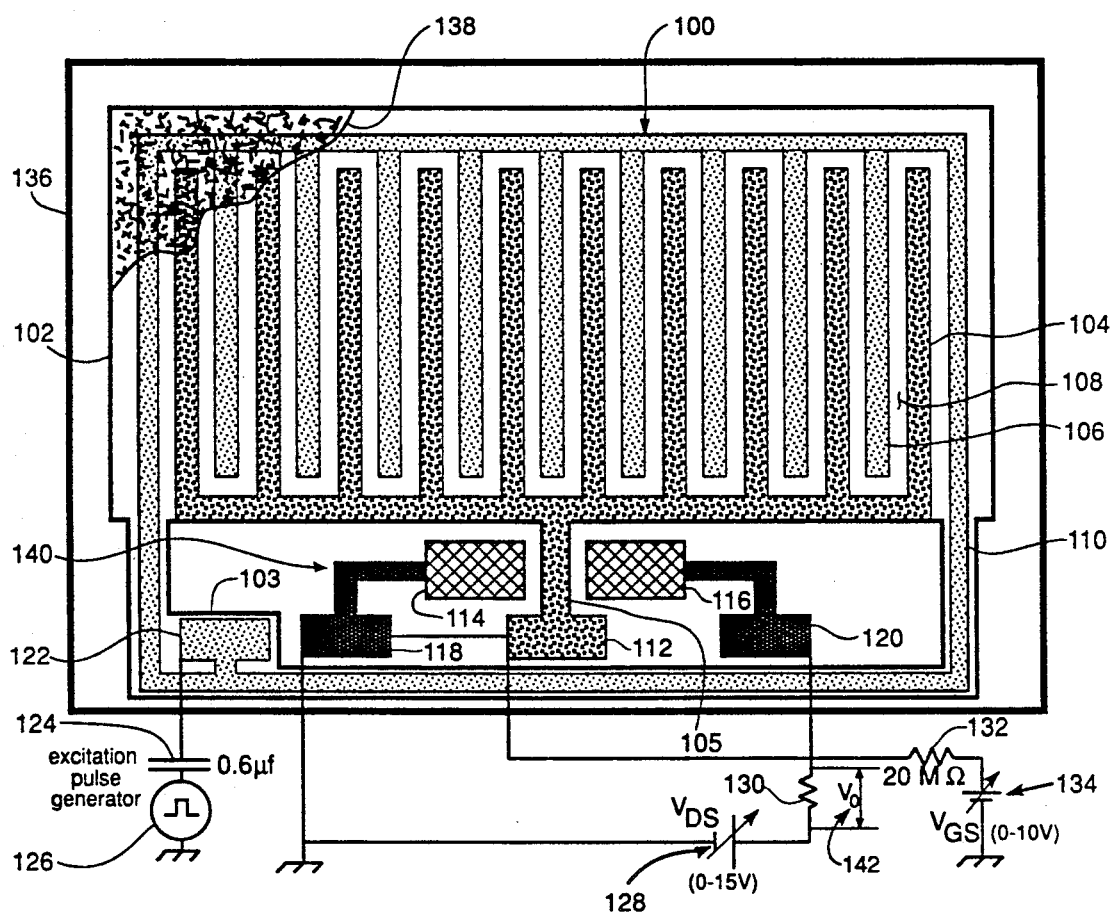
FIG. 1 shows details of a chemiresistive sensing element according to the invention.

FIG. 1 in the drawings shows an interdigitated gate electrode field effect transistor (IGEFET) 140 that is signal coupled to an electron-beam evaporated copper phthalocyanine (CuPc) thin film 138. In the FIG. 1 sensor arrangement, changes in the molecular structure or the chemical composition of the thin film shown in cutaway representative form, at 138 in FIG. 1, are used to change the output signal of the amplifier stage which is embodied in the form of the field effect transistor 140. The thin film 138 is capable of selective detection of parts-per-billion (ppb) concentrations of gaseous pollutants such as nitrogen dioxide and DIMP.

The thin film 138 in FIG. 1 sensor is preferably fabricated from a copper phthalocyanine material. Other materials from the metal-substituted phthalocyanine family, including the metals Ag, Co, Fe, Mg, Mn, Na, Ni, Pb, Pd, Pt, and Zn, are possible substitutes for the preferred copper in the FIG. 1 sensor—especially in sensors for other challenge gases. The electrical conductivity of metal-doped phthalocyanine material films has been observed to increase upon exposure to electron acceptor challenge gases such as Boron Chloride, Boron Flouride, Chlorine, Nitrogen Dioxide, and organophosphorus compounds. Copper phthalocyanine, in particular, is characterized by low proton affinity, good resistance to dissolution by concentrated mineral acids, and sublimation at temperatures as high as 580° C. without decomposition. This desirable stability performance has been attributed to the magnetic and electron spin resonance associated with the included copper-nitrogen double bond. The strong electron donor sites that comprise the planarly delocalized $\Pi$-electron system in CuPc thin films has been postulated to be responsible for the experimentally observed electron-acceptor gas exposure interactions and the corresponding electrical conductivity changes experienced in this material. Since nitrogen dioxide is reversibly adsorbed on heated copper phthalocyanine films at temperatures in the 100°-170° C. range, the interaction site for this material has been identified to be at the film's intercrystallite interfaces, rather than involving a true bulk diffusion mechanism.

The interaction between copper phthalocyanine films and an electron accepter gas is likely to result in a coordination bond; that is, a bond whose energy is stronger than a purely adsorptive interaction, or less than 40 KJ/mole, but weaker than a true covalent bond and its approximately 300 KJ/mole energy. In the present invention, both nitrogen dioxide and DIMP are found to be reversibly adsorbed on the copper phthalocyanine film with nitrogen dioxide introducing a stronger electrical interaction for an identical exposure concentration.

Considering now additional details of the FIG. 1 apparatus, the sensor in FIG. 1 is comprised of the interdigitated electrode structure, indicated at 100, in combination with the physically adjacent field effect transistor 140. The transistor 140 may be of the conventional metal-oxide-semiconductor field effect design, or MOSFET type, with the electrode structure 100 coupled to the gate terminal thereof. The interdigitated electrode structure 100 is composed of a driven electrode array indicated at 106 in FIG. 1 and the guard ring element 110. The guard ring is shown to envelope the entire sensor in order that it function as a stray surface current leakage blocking device.

The floating electode portion of the interdigitated gate structure 100 is indicated at 104 in FIG. 1 and is shown to be connected to the gate region 105 of the transistor 140. The interdigitated electrode structure 100 is provided with a high-degree of electrical isolation between the driven electrode array 106 and the floating electrode array 104 by way of fabrication of the interdigitated array on a highly-insulating silicon dioxide layer 108. The physical extent of the silicon dioxide substrate for the interdigitated array is indicated at 102 in the FIG. 1 drawing. It is notable in FIG. 1 that the silicon dioxide substrate extends also under the conductive paths which connect with the pad 122 as is shown at 103 in FIG. 1. With a one micron thickness of thermally-grown silicon dioxide, having resistivity greater than $10^{14}$ ohm.centimeters, an electrical isolation between the arrays 104 and 106 of greater than 100 megohms is possible.

The transistor 140 may be designed using the commercially available Metal Oxide Semiconductor Implementation Service (MOSIS) 3-micrometer, p-well, double-metal, complementary-metal-oxide-semiconductor (CMOS) technology design aid sequence or similar techniques. The MOSIS service is available from Information Science Institute, University of Southern California (USC/ISI), Marina del Rey, Calif. with release 3.0 being current at the time of writing. Additional related information is to be found in "Principles of CMOS VLSI Design—A Systems Perspective" a textbook authored by Neil Weste and Kamran Eshraghian and published in 1985 by Addison-Wesley of Reading, Mass. Preferably an identical reference transistor, which is not shown in FIG. 1, is located adjacent the transistor 140 in order to facilitate post-fabrication performance characterization and subsequent monitoring of the operating stability in the sensor cell. A p-well may be used to enhance electrical isolation between the interdigitated electrode structure and the transistor 140.

The transistor 140 is preferably of the n-channel enhancement-mode type. Gold or aluminum are preferred for use in the interdigitated electrode array and in the bonding pads of the transistor 140; that is, the pads shown at 112, 118, 120 and 122 in the FIG. 1 structure. The overall dimensions of the FIG. 1 device are preferably on the order of 4466×6755 micrometers with other significant dimensions and data being indicated in Table 1 below. Excepting for the regions of the interdigitated gate structure and the bonding pads, the topmost surface of the FIG. 1 sensor is preferably passivated with a one micrometer thick layer of chemically-vapor deposited silicon dioxide.

TABLE 1

| SIGNIFICANT DIMENSIONS/DATA FOR FIG. 1 IGEFET SENSOR | |
|---|---|
| STRUCTURE | NUMERIC VALUE |
| Interdigitated Gate Electrode | |
| Number of fingers in the floating-electrode | 29 |
| Number of fingers in the driven-electrode | 30 |
| Electrode finger width ($\mu$m) | 7.5 |
| Electrode finger separation ($\mu$m) | 9.0 |
| Interdigitated electrode array length ($\mu$m) | 3792 |
| Interdigitated electrode array width ($\mu$m) | 921 |
| MOSFET Active gate length ($\mu$m) | 12 |
| MOSFET Active gate width ($\mu$m) | 15 |
| Phthalocyanine film thickness (angstroms) | 70–1,000 |

The copper phthalocyanine chemically reactive film 138 is of the high-purity (99.9% purity) type and is fabricated from materials available from such suppliers as Fluke Chemical Corporation of Ronkonkoma, N.Y. The film 138 is preferably deposited on the dielectric supported interdigitated electrode structure 100 using a helium cryogenically-pumped, electron-beam thermal evaporation process at a pressure of $10^{-6}$ Torr vacuum. An etched metal mask may be used to confine the deposited copper phthalocyanine thin film within the boundaries of the interdigitated electrode structure. Nominal film thicknesses on the order of 70-1,000 angstroms may be used and may be verified using a precalibrated quartz crystal microbalance positioned coplanar with the interdigitated electrode structure. Films of other thicknesses may have certain performance advantages in the FIG. 1 apparatus as is described below. The FIG. 1 sensor may be mounted in a standard 300 mil cavity size, 64-pin dual-in-line integrated circuit package of the type supplied by Kyocera Corporation of Edina, Minn., as part #KD83578, for example. Other details of the transistor 140 shown in FIG. 1 include the drain contact structure 116 and the source contact structure 114.

The sensor in FIG. 1 is preferably operated at a fixed temperature, such as 125° C. and is enclosed by a housing which enables convenient delivery of the challenge gas and also the purge gas to the film 138. The temperature control apparatus and housing for the sensor cell of FIG. 1 may be in accordance with the arrangement of such apparatus as is known in the art or may be in accordance with the apparatus described in my previously published paper "Organophosphorus Compound Detection with a Supported Copper+Cuprous Oxide Island Film. 1. Gas—Sensitive Film Physical Characteristics and Direct Current Studies", which was published with R. M. Walser, appearing in Analytical Chemistry, volume 60, pages 1731-1736, 1988, the contents of which are hereby incorporated by reference herein. A manifold structure as known in the art may also be used to facilitate switching between the various challenge and purge gases.

The electrical components shown in connection with the sensing cell in FIG. 1 provide the signal coupling and characteristic curve operating point determinations needed for the transistor 140. These electrical components include the direct current supplies 128 and 134, which are indicated as variable voltage batteries; the current-limiting resistance 132 connected between the transistor gate and the gate biasing direct current supply 134; and the drain load resistance 130 which is coupled to the drain to source biasing direct current supply 128. The output signal ($V_o$) for the transistor 140, of course, appears across the resistance 130 as is indicated at 142 in FIG. 1. The excitation pulse generator circuit for the interdigitated and thin film covered electrode array is indicated at 126 in FIG. 1; as described below, this source is preferably arranged in the form of an impulse-like pulse generating circuit. Any direct current signal component present in the signal from the excitation generating circuit 126 is blocked by the coupling capacitor 124 which is located between the excitation generating circuit and the driven component 106 of the interdigitated electrode array.

The use of high-impedance loading for the interdigitated chemiresistor portion of the FIG. 1 sensing cell is a desirable feature of the FIG. 1 apparatus. Both the desire for this high-impedance loading and the need to minimize stray signal coupling and stray leakage into the signal coupling paths suggest the FIG. 1 arrangement of using a field effect transistor as the chemiresistor element's load and also make the physical disposition of this transistor in close proximity with the chemiresistor cell a desirable arrangement. As a result of the negligible current flow into the gate terminal of a field effect transistor, the effective input impedance of the transistor 140, that is, the load presented to the chemiresistor portion of the FIG. 1 cell, is essentially the value of the current-limiting resistance 132, or 20 megohms. Other amplifier arrangements which achieve this desired high-impedance loading are, of course, possible and may be arranged by persons skilled in the electronic art. According to one other such arrangement, the transistor 140 could be replaced with a high-input impedance multiple transistor amplifier circuit, such as an operational amplifier, having its positive input terminal connected to the chemiresistor cell. Similarly, with the use of high quality connecting cables, a remote location for the transistor 140 may also be feasible.

When fabricated according to the above described features, transistors of the type shown at 140 in FIG. 1 are found to be capable of low-frequency gains in the range of 11 to 13 dB. This characteristic may be measured with instruments such as the model 4145 semiconductor parameter analyzer available from Hewlett-Packard Corporation of Palo Alto, Calif. With a gate to source voltage ($V_{GS}$) of ten volts, the MOSFET transistor provides transconductance or gm values in the range of 0.133 mhos. With a gate bias of 2.5 volts, the drain-to-source on-resistance of the transistor 140 ($r_D$) is in the range of 130 kilohms. With these values of gm, $r_D$, and a 100 kilohms drain bias resistor 130 in FIG. 1, the direct current gain of the MOSFET may be calculated to be in the range of 15 dB. By way of comparison, the gain of the above referred-reference MOSFET devices fabricated concurrently with the transistor 140 is found to be one dB greater than these values, a condition which may at least partially be explained by the difference between the two gate electrode geometries. The three-dB cutoff-frequency of a MOSFET of the type shown at 140 in FIG. 1 is found to be on the order of 10 kilohertz with the phase-lag characteristic decreasing from 180 degrees at low frequencies to nearly 90 degrees at a frequency of 100 kilohertz.

The chemically-active thin film 138 is controlling of the transistor 104 operation in the FIG. 1 apparatus. In order to selectively detect physiologically detrimental concentration levels of an organophosphorus chemical warfare nerve agent, a challenge gas must induce a measurable electrical response in the FIG. 1 polymeric thin film 138 while in the presence of other interfering species. In the FIG. 1 detector, this requirement implies that the sensor's output response signal, which may include contributions arising from several different gaseous species, nevertheless possesses a dominant contribution from the primary species which include, $S_x$, (that is, the organophosphorus chemical warfare nerve agent or analog compound) relative to that of the interfering species, $S_i$. That is, an explicit form of the well known Eisenmann-Nikolskij equation, which is recited, for example, in the article "Chemical Selectivity of Field Transistors", in "Sensors and Actuators", volume 12, pages 121-128, 1987 and authored by J. Janata; when cast in terms of the sensor's output voltage response signal ($V_o$) and equilibrium constant, ($K_{i,x}$ is:

$$V_o = V(S_x \Sigma K_{i,x} S_i).$$

Further, the interaction of the species of interest, $S_x$, with the chemically-active polymeric thin film can be expressed in terms of a general equilibrium equation involving its equilibrium constant $K_x$. That is, $$S_x + \text{Chemically-active thin film}$$

$$K_x \Longleftrightarrow [S_x \cdot \text{Chemically-Active Thin Film}]$$

and $$\Delta G_x^\circ = -RT\ln(K_x)$$

where $\Delta G_x^o$ is the Gibb's free energy, R is the universal gas constant and T is the absolute temperature in degrees Kelvin. Further, the Gibb's free energy ($\Delta G_x^o$) is composed of enthalpic ($\Delta H_x^o$) and entropic ($-T\Delta S_x^o$) energy contributions, given by:

$$\Delta G_x^o = \Delta H_x^o - T\Delta S_x^o.$$

For a selective response, the Gibbs's free energy, $\Delta G_x^o$, for the species of interest, $S_x$, must be greater than that for any interfering species, $S_i$, or combination thereof ($\Sigma K_i, xS_i$). Thus, the chemical and thermodynamic selectivity performance feature requires a large negative value of the interaction enthalpy or a large positive value of the interaction entropy for the species of interest, or both.

In the context of the detector described herein, the chemical and thermodynamic selection rule can be optimized for a system where the species of interest chemisorbs on the surface of the chemically-active polymeric thin film. Since the chemical and thermodynamic interaction energies are inversely proportional to the interaction distance separating the species of interest and the chemically-active polymer (typically on the order of 5 to 50 angstroms), this requirement implies that the interacting molecule has to approach the binding site very closely. This situation will occur only if the shape of the interacting molecule fits the shape of the available binding site.

Finally, if the interaction is highly selective, the short-range interactions will combine in a cooperative manner to produce a large response signal, meaning that the individual, relatively weak, short-range interactions favorably combine to yield an overall strong interaction relative to the net response of all the other competing species (that is, the interferants). This requirement can only occur if the interaction moieties possess a precisely defined spatial orientation. One such system involving the metal-doped phthalocyanine semiconducting polymers and the organophosphorus chemical warfare agents and their analog compounds (such as DIMP) and is disclosed by Robert L. van Ewyk, Alan V. Chadwick, and John D. Wright, in the article "Electron Donor-Acceptor Interactions and Surface Semiconductivity in Molecular Crystals as a Function of Ambient Gas", appearing in the Journal of the Chemical Society, Faraday Transactions I, Vol. 76, No. 10, pp 2194-2205, 1980.

The metal-doped phthalocyanines possess several additional properties which make them attractive for toxic gas detection. They are relatively good electrical conductors with resistivity on the order of $10^{11}$ ohm-centimeters, are stable at temperatures up to 450° C., and can be deposited as thin films by vacuum thermal sublimation or Langmuir-Blodgett techniques. Ewyk et al, have established that the phthalocyanines are hole (p-type) conductors and are suitable for detecting electron-accepting gases, such as nitrogen dioxide. A similar suitability appears to exist for DIMP. The conductivity enhancement observed when the electron-accepting gas adsorbs on the polymer's surface involves an electrophillic interaction with the extensive $\pi$-orbital system of chemical bonds in the metal-doped phthalocyanine molecule.

When an electron-accepting gas molecule is chemisorbed on the metal-doped phthalocyanine thin film, the adsorption site becomes negatively charged. This situation increases the localized hole concentration in the metal-doped phthalocyanine thin film. As a result, with all localized hole concentration contributions considered, the overall conductivity of the metal-doped phthalocyanine thin film increases. Of special interest in the herein described sensor, the metal-doped phthalocyanine polymers also demonstrate a significant selectivity and sensitivity to the organophosphorus chemical warfare nerve agent analog compound, diisopropyl methylphosphonate (DIMP) and similar agents at operating temperatures on the order of 120°-150° C. The chemical interaction kinetics are governed by the well-known Elovich rate equation (see the Robert L. van Ewyk et al 1980 article cited above).

Since the conductivity enhancement effect is predominantly a surface phenomenon, ultra-thin films are specifically desired; films on the order of 70-130 angstroms thick. This thickness specification minimizes the contribution of the material's bulk absorption effects and, in a synergistic fashion, further manifests its desirability through the sensor's reversibility performance feature. That is, if thick metal-doped phthalocyanine films of thickness greater than 500 angstroms, are exposed to DIMP at 120-150 degrees Celcius the reversibility time of the sensor will be on the order of several tens of minutes (usually at least twenty minutes). On the other hand, the reversibility of an ultra-thin film of this specification is typically less than two minutes. Further, since vacuum thermally sublimated films yield a disordered metal-doped phthalocyanine thin film, the Langmuir-Blodgett deposition technique is preferred because it yields mono- and bimolecular layers possessing a highly-ordered structure. This well-defined morphological feature readily facilitates both the adsorption and desorption of the DIMP molecule, and is manifested by a further shortening of the reversibility time, thereby times typically less than one minute are achievable.

Figure 2A:
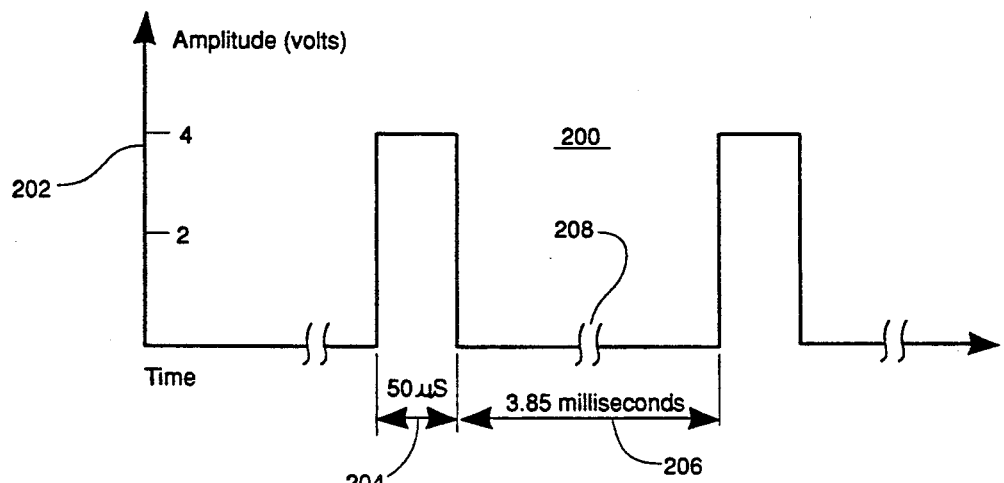
FIG. 2a shows an impulse-like (square-wave approximation) excitation form useable in the FIG. 1 sensing element.

FIG. 2a in the drawings shows specific details of a signal which may be used to simulate the impulse function desired for exciting the chemiresistor portion of the FIG. 1 sensing cell, that is, an arrangement of the signal generated by the source 126 in FIG. 1. With respect to this FIG. 2a signal, the theoretical aspects of the impulse signal, especially the broad spectrum of sinusoidal components included in a signal of this nature, are well known in the electrical art. One description of the impulse signal appears in the text "Information Transmission Modulation and Noise" authored by Mischa Schwartz and published by McGraw Hill Book Company which is hereby incorporated by reference herein. Section 2-11 of the Schwartz text is, for example, relevant to this signal. A mathematically precise embodiment of an impulse function signal includes a pulse of infinitely great amplitude and infinitely short pulse duration. However, practical implementations of this type of excitation are necessarily compromised in reality. One such practical compromise signal which is found to provide acceptable signals for the FIG. 1 apparatus is the signal 200 in FIG. 2a. As indicated by the scale 202 in FIG. 2a, the signal in FIG. 2a is provided with an amplitude in the range of 4 volts, such signal amplitude is convenient for electronic generation and for use in the transistor 140. In keeping with the desired small pulse width of an impulse function signal, the pulse duration of the FIG. 2a signal as indicated at 204, is preferably made to be some brief duration such as the indicated 50 microseconds; the interval between pulses is made to be significantly longer as is indicated by the 3.85 millisecond time between pulses which is indicated at 206. The relative scales of the 50 microsecond and 3.85 millisecond time intervals are distorted in FIG. 2a as is indicated by the break lines 208. Signals of the type indicated in FIG. 2a are within the capability of commercially available pulse or function generator instruments. a Wavetek Corporation model 148 function generator, for example, may be used as the FIG. 1 signal source 126. The Wavetek instrument is manufactured by Wavetek Corporation of San Diego, Calif.

Figure 2B:
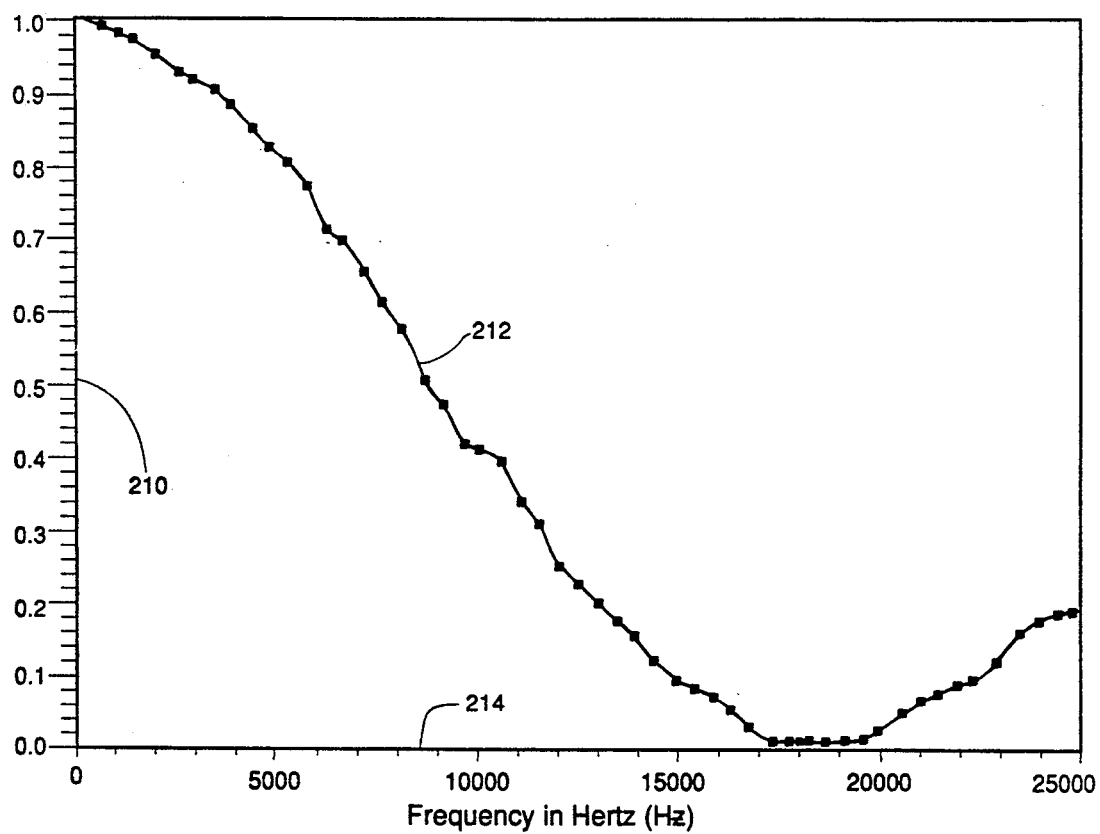
FIG. 2b shows its Fourier transformation waveform.

The FIG. 2b portion of FIG. 2 shows the normalized Fourier transform function for the FIG. 2a excitation pulse (square wave) signal. The Fourier transform function at 212 is displayed on a vertical scale of relative magnitude indicated at 210 relative to a horizontal scale of frequency having units of Hertz as indicated at 214 in FIG. 2b. Data points along the Fourier function 212 are spaced at 480 Hertz frequency intervals in FIG. 2b. As is explained in greater detail below, the recognition of gaseous components in a challenge gas with the present invention involves a subtractive data manipulation of both the FIG. 2b Fourier function and the related signals to be generated from the output of the FIG. 1 sensing cell.

Figure 4:
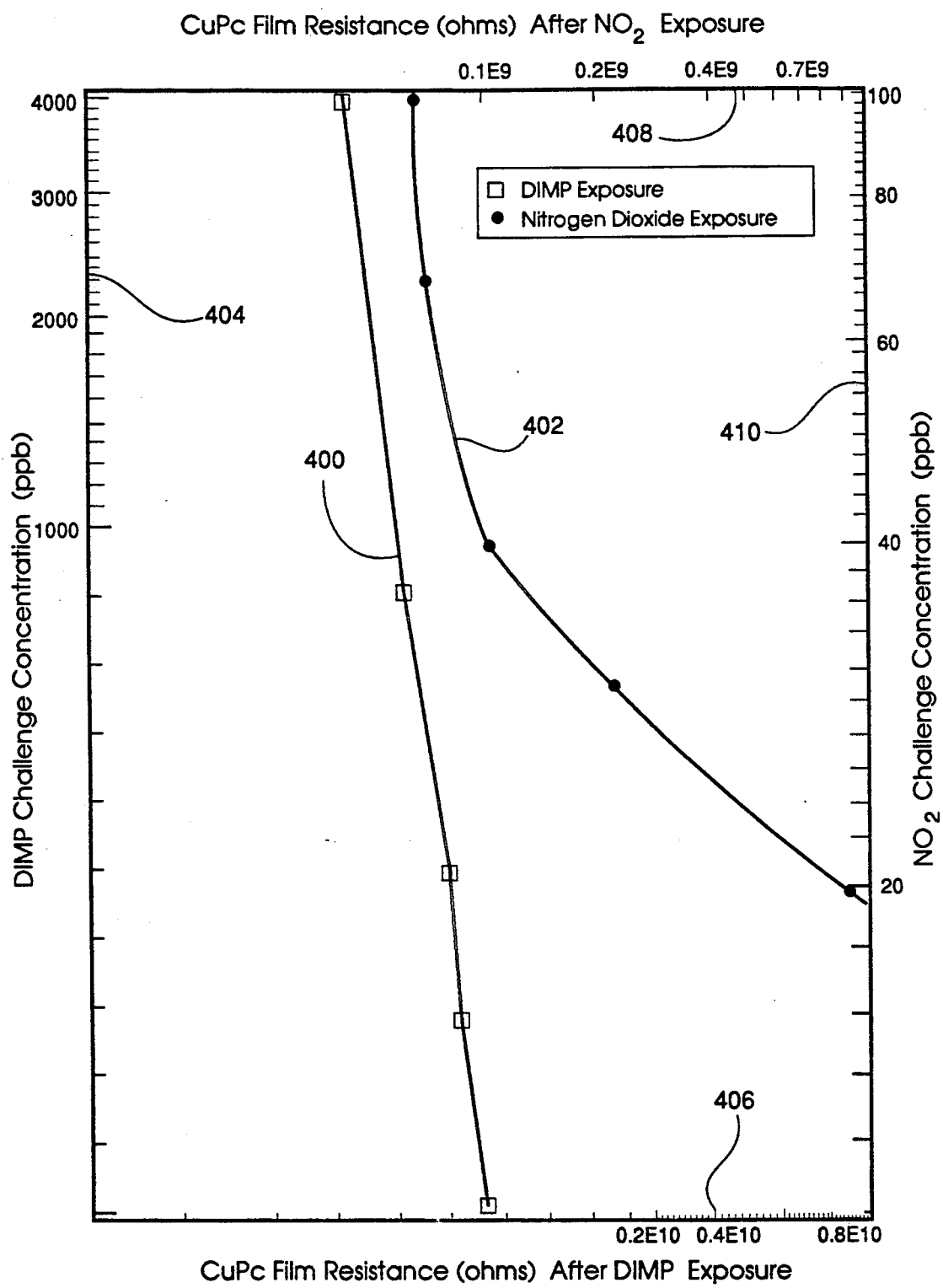
FIG. 4 shows the direct current resistance change expected in a FIG. 1 sensor in response to two exemplary challenge gas components.

FIG. 4 in the drawings shows the direct current electrical resistance of a FIG. 1 type chemiresistor when exposed to different concentrations of the herein referred-to DIMP and nitrogen dioxide challenge gases. The FIG. 4 data represents nitrogen dioxide and DIMP concentrations in the range of 20 to 400 parts-per-billion (ppb) and 40 to 4000 parts-per-billion (ppb) respectively as shown along the scales 404 and 410. These FIG. 4 resistance values are shown on the scales 406 and 408 and represent characteristics occurring at a 125° C. temperature and with a thickness of the film, 138 in FIG. 1, of 1000 angstroms.

The data in FIG. 4 is a result of a sequence of exposing events with the times for purging and exposing being artificially elongated to 20 and 30 minutes of duration in order to assure the attainment of an equilibrium response.

In obtaining the curves 400 and 402 in FIG. 4, it is to be noted that the chemiresistor of FIG. 1 may not provide reproducible data values during the first three cycles of an exposure and purge sequence; however, after these early fluctuations, rapid convergence toward a set of reproducible initial, final and delta resistance values is achieved. Consequently, preconditioning of the phthalocyanine films using a sequence of three 30-minute duration low-concentration level exposure and purge cycles is desirable for the FIG. 1 sensor cell. It is also observed that the time required to attain equilibrium initial and final resistance values in a FIG. 1 type of chemiresistor may be expected to decrease after the preconditioning process is accomplished.

For both of the typical challenge gases considered herein, the resistance of the FIG. 1 film rapidly decreases and can be expected to achieve 63% of its final value during the first 3 minutes of an exposure cycle. Afterwards, the resistance of the film can be expected to decrease toward an equilibrium value, but at a much slower rate. Upon purging of the challenge gas, the film's resistance rapidly increases during the first five minutes of time to achieve 63% of its final value. Afterwards, the resistance continues to increase toward an equilibrium value, but also at a much slower rate.

The film equilibrium values resulting from DIMP exposure are essentially linear over the FIG. 4 identified concentration range. The resistance values for the more electro-negative and physically smaller nitrogen dioxide challenge species are, however, both nonlinear and attended by an increased resistance change to gas concentration sensitivity. From the slopes of the least-squares fitted nitrogen dioxide and DIMP exposure representing plots, it can be surmised that an 800 parts-per-billion (ppb) DIMP challenge concentration would be required to induce an equivalent resistance change to that expected for a 30 parts-per-billion (ppb) nitrogen dioxide challenge concentration.

The preconditioning behavior described above suggests that during an exposure, the challenge gases displace less tightly bound gaseous species, such as oxygen, at the surface of the phthalocyanine film. This characteristic and the observed shortening of the time increment required to obtain a reversible response is consistent with the heterogeneous intercrystallite interface surface site adsorption model discussed herein. In view of this kinetically limited adsorption behavior, use of isothermal preconditioning of the FIG. 1 chemiresistor and the above described pulsed-mode sampling of the challenge gases is desired; that is, the preconditioning and purging cycle described herein, are desirable in order to accommodate the variable response time needed to achieve a thermodynamic equilibrium surface coverage condition.

Figure 3:
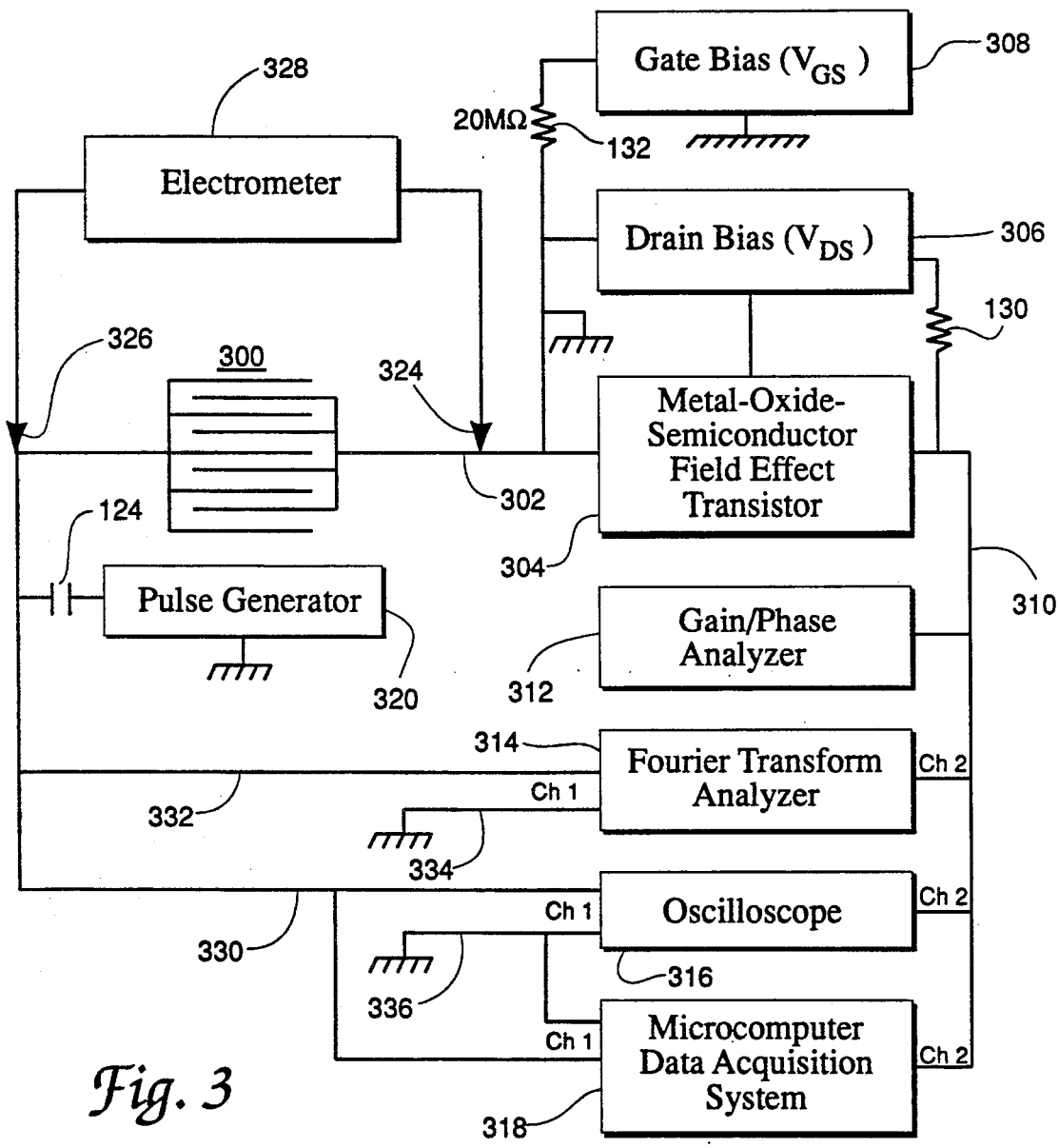
FIG. 3 shows the components of a challenge gas detection and measuring system which employs the FIG. 1 sensor element.

FIGS. 5 and 6 in the drawings show a series of voltage waveforms obtained with the FIG. 1 sensor apparatus in response to a plurality of exposures of the nitrogen dioxide challenge gas-in the FIG. 5 waveforms, and the DIMP challenge gas-in the FIG. 6 waveforms. The apparatus used in obtaining the FIGS. 5 and 6 waveforms, and also used in obtaining the data plots of FIG. 4, is shown in FIG. 3 of the drawings and is described in a later portion of this specification.

The waveforms shown in the lower portions of each view in FIGS. 5 and 6 are measured across the 100 Kilohm output load resistance shown at 130 in FIG. 1 and were collected following a series of 30-minute duration exposure and purge cycle events and preconditioning with low-level challenge gas exposure as described above. Following the nitrogen dioxide exposure which results in the FIG. 5 data, a 24-hour purge sequence was employed before the DIMP exposure for the waveforms of FIG. 6 were collected. A copper phthalocyanine film is used at 138 in FIG. 1 for each of the FIG. 5 and FIG. 6 waveform sequences. In the six views of FIG. 5 and in the six views of FIG. 6, that is, in FIGS. 5a–5f and in FIGS. 6a–6f, the upper-most pulse waveform defines the signal applied to the bonding pad 122 in FIG. 1; that is, the signal originating in the source 126 and applied to the driven electrode of the electrode structure 100. The lower waveform in each of these FIG. 5 and FIG. 6 views represents the FET transistor amplified output of the thin film interdigitated electrode structure 100 in FIG. 1 in response to the different challenge gas or purge gas exposures. The purge gas exposures are shown in the left-most or FIGS., 5a, 5c, and 5e views in FIG. 5, and similarly, in the views of FIGS. 6a, 6c, and 6e in FIG. 6.

Figure 5A:
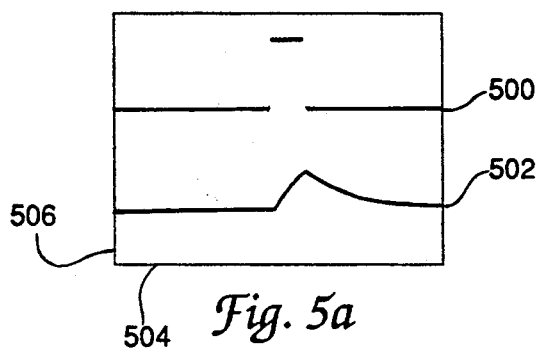
FIGS. 5a through 5f show a plurality of sensor element time-domain responses to varying nitrogen dioxide challenge gas concentrations.
Figure 5B:
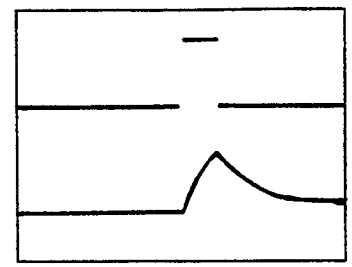
Figure 5C:
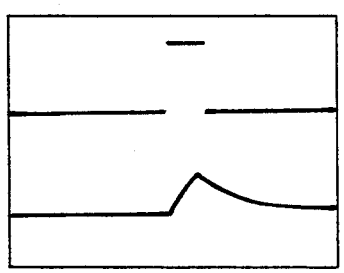
Figure 5D:
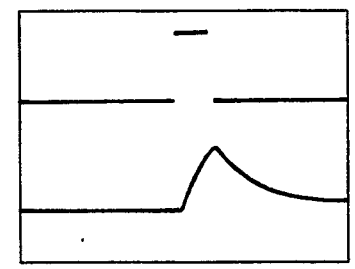
Figure 5E:
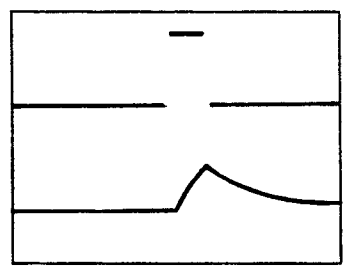
Figure 5F:
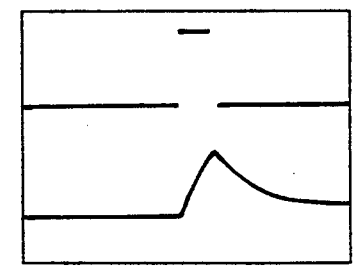
Figure 6A:
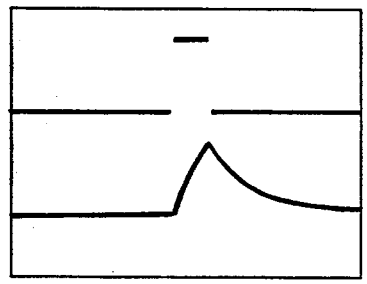
FIGS. 6a through 6f show a plurality of sensor element time-domain responses to varying DIMP challenge gas concentrations.
Figure 6B:
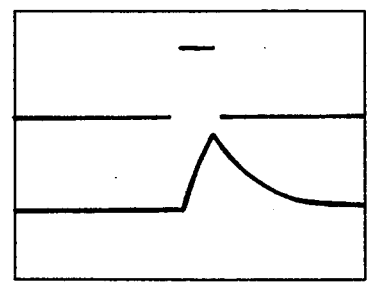
Figure 6C:
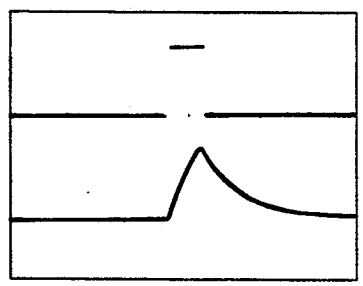
Figure 6D:
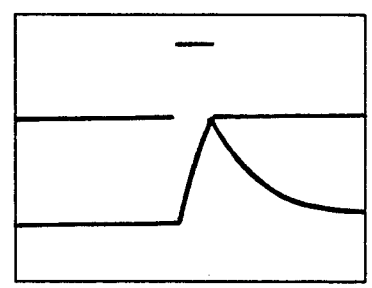
Figure 6E:
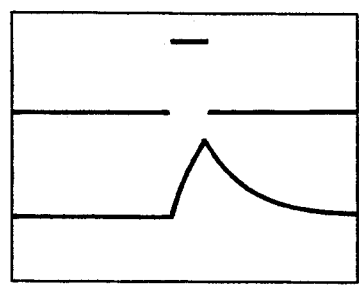
Figure 6F:
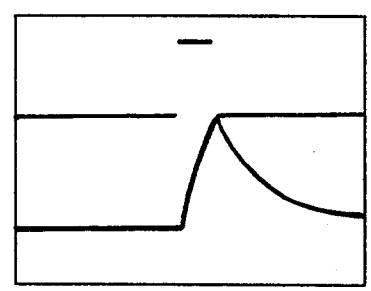

In FIG. 5a, for example, the lower waveform 502 represents sensor exposure to ambient air following a preconditioning sequence while the lower waveform in FIG. 5b represents exposure to a 100 parts-per-billion concentration of nitrogen dioxide. The lower waveform in FIG. 5c represents a succeeding purge with ambient air, and the lower waveform in FIG. 5d represents a 200 parts-per-billion nitrogen dioxide exposure. In a similar manner, the lower waveform in FIG. 5e represents a purge with ambient air and the lower waveform in FIG. 5f represents an exposure to 400 parts-per-billion nitrogen dioxide. Similarly in FIG. 6 the lower waveforms of FIGS. 6b, 6d and 6f represent exposures to challenge gases containing a 100 parts-per-billion DIMP component, an 800 parts-per-billion DIMP component, and a 4000 parts-per-billion DIMP component, respectively. The waveforms of FIGS. 6a, 6c, and 6e in a similar manner represent the preceding and intervening purges with ambient air.

In each of the FIG. 5 and FIG. 6 views, the upper waveform, that is, the interdigitated array excitation pulse, is shown on a horizontal scale with 4 volts-per-division; and a vertical scale with 50 microseconds-per-division; the excitation pulse is thereby shown to have an amplitude of 4 volts and a duration of 50 microseconds. For each of the lower waveforms in FIGS. 5 and 6, the vertical scale indicated at 506 is 0.2 volts-per-division and the horizontal scale is the same 50 microseconds-per-division. The disconnected appearance of the upper waveform pulses in FIGS. 5 and 6 results from their laboratory instrument source, the fast rise time of these pulses, and the well known in the art inability of oscilloscope cathode ray tube phosphors to respond with equal brilliance to fast and slow waveform writings.

Although the time-domain responses for each of the challenge gas mixtures in the waveforms of FIGS. 5 and 6 are indeed different, as is exemplified by the different amplitudes and slopes in the lower waveform, a meaningful criterion for differentiating between different gas concentrations and different gas species acting on the sensor thin film element is not readily apparent from the FIGS. 5 and 6 waveforms. This ambiguity is attributable to the major similarities in the waveforms for different concentrations and gaseous species. To improve upon this lack of distinction, a signal processing technique is employed in the present apparatus wherein the magnitude of the normalized difference Fourier transform of the waveforms of FIGS. 5a and 5b is used to provide a clear distinction between sensor output waveforms.

Since the relative slopes of the leading and trailing edges in the lower waveforms of the FIG. 5 and FIG. 6 views are distinct, and furthermore, because the peak of each of these response waveforms changes for different exposure concentration, it has been found that Fourier's theorem may be applied to determine the ensemble of frequency components that determine the lower waveform's time-domain dielectric relaxation response. The time-invariant and reversible behavior of the copper phthalocyanine to the nitrogen dioxide and DIMP challenges are enabling of this signal processing arrangement because it provides a common base-line for comparing normalized difference spectra. Normalization in the sense used here means, of course, that the waveforms are confined to a consistent and common vertical axis scale by way of dividing their amplitude values at each time location by the peak amplitude found in the spectrum of the waveform. According to this arrangement, each considered waveform will have a peak normalized amplitude of 1.0 with the other waveform values being scaled downward from this peak value so as to also maintain the original shape of the waveform.

Figure 7:
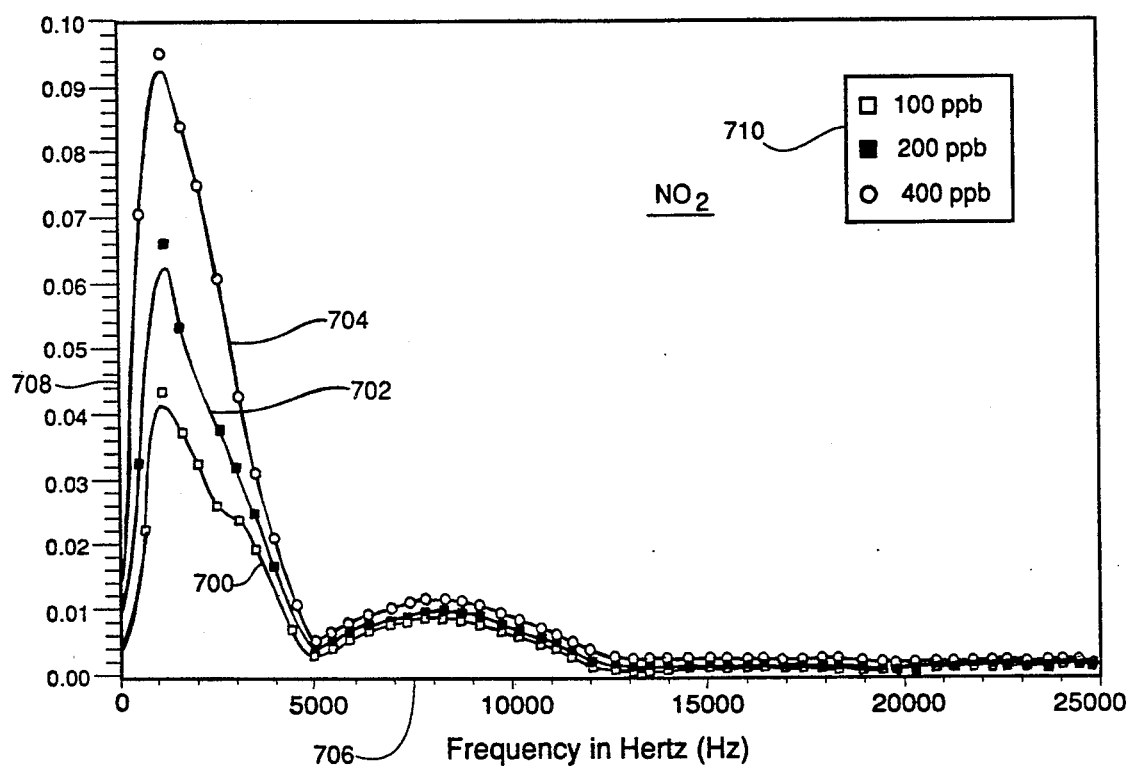
FIG. 7 shows normalized Fourier transformed difference waveforms for the nitrogen dioxide challenge gas concentrations in FIG. 5.

The normalized difference Fourier transform spectra associated with each of the FIGS. 5b, 5d, and 5f challenge gas concentrations is shown in FIG. 7 of the drawings. In FIG. 7, the curves 700, 702, and 704 represent the respective different challenge gas concentrations-in accordance with the legend shown at 710 and with numeric values as indicated along the vertical and horizontal scales 708 and 706 in FIG. 7. In a similar manner, the normalized Fourier transform spectra associated with the DIMP challenge gas waveforms of FIGS. 6b, 6d, and 6f are shown respectively in the curves 800, 802 and 804 of FIG. 8 in accordance with the legend 810 and with amplitudes and time features as measured along the vertical scale 808 and the horizontal scale 806.

Figure 8:
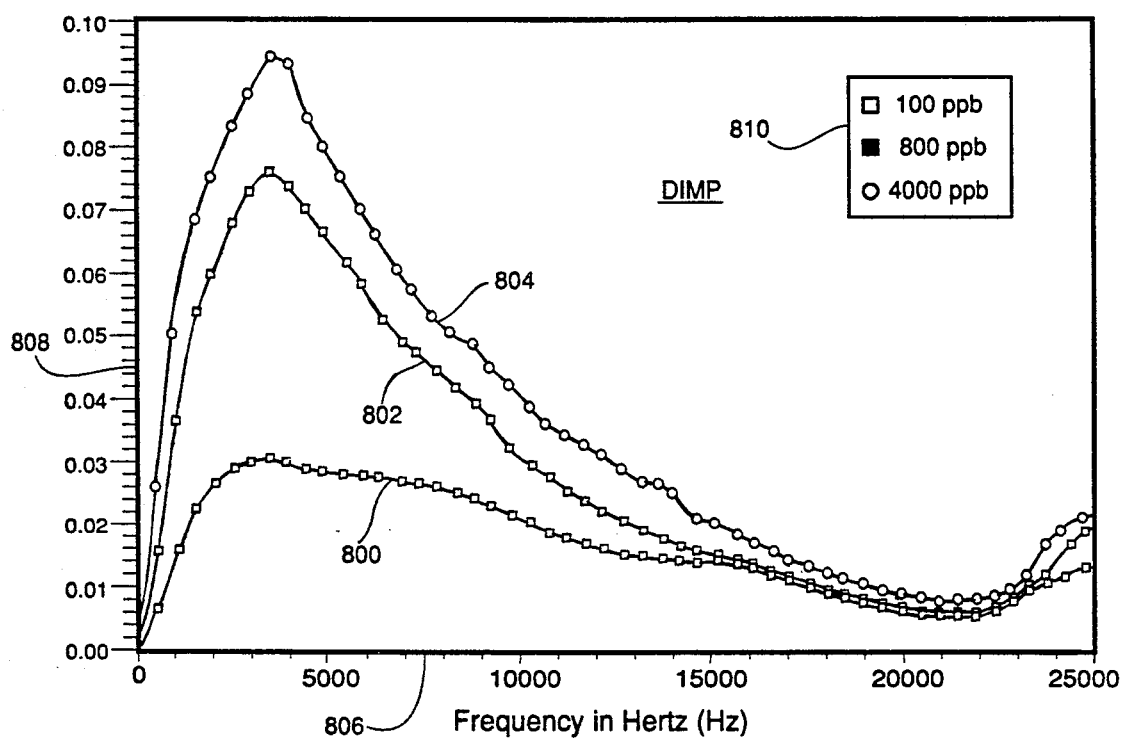
FIG. 8 shows normalized Fourier transformed difference waveforms for the DIMP challenge gas concentrations in FIG. 6.

Clear distinction between the curves in FIGS. 7 and 8 are readily discernable, for example, the first peak of the nitrogen dioxide response occurs at a frequency of approximately 1000 Hertz while the first peak for the DIMP response occurs at approximately 3400 Hertz. Additionally, the rise and decay rates associated with these first peaks are more pronounced in the case of the nitrogen dioxide spectra. Both the nitrogen dioxide and DIMP spectra also contain a secondary peak with the nitrogen dioxide secondary peak occurring at approximately 8200 Hertz, while the DIMP secondary peak occurs in the range of 25 kilohertz.

These relatively low-frequency resonant peaks also suggest that a long-range dielectric polarization interaction is being facilitated by the adsorbed challenge gases in the FIG. 1 sensing cell. Qualitatively, the electronic and steric features of the challenge gases, along with the interstitial crystallite adsorption model discussed earlier, are postulated to account for the observed interfacial dielectric relaxation behavior. The heterogeneous nature of the challenge gas adsorption process and the disordered grain-boundary nature of the copper phthalocyanine films require an extended set of data in order to quantitatively treat the interaction mechanism present in the FIG. 1 sensor cell.

FIG. 3 in the drawings shows one arrangement for an apparatus that is capable of characterizing the challenge gas exposure performance of a sensor cell of the type shown in FIG. 1. The apparatus of FIG. 3 may also be used in the collection of challenge gas identification data of the type shown in FIGS. 5, 6, 7, and 8 herein. In the FIG. 3 apparatus, the interdigitated thin film sensor of FIG. 1 is shown at 300 while the transistor 140 in FIG. 1 is represented at 304 and the transistor biasing components shown in the lower portion of FIG. 1 are indicated at 306 and 308. The signal from the thin film and interdigitated electrode structure 300 is communicated to the transistor 304 by way of the path indicated at 302, this path representing the short interconnection between the transistor's gate and floating array electrode elements in FIG. 1. The pulsed excitation signal source, that is, the impulse-like excitation for the thin film and interdigitated electrode structure is shown at 320 in FIG. 3 and is presumed to provide an impulse-like signal such as the 4-volt peakamplitude and 50-microsecond duration 256 hertz repetition frequency signal described above and shown in FIG. 2a.

The output signal of the transistor 304, that is, a signal appearing across the load resistance 130 in FIG. 1 is applied to the array of signal processing instruments indicated at 312, 314, 316, and 318 in FIG. 3 by way of the communication path indicated at 310. Since the desired Fourier transform data is a subtracted signal, that is, the difference between the thin film detector cell input and output signals, the input signal to the detector cell is also provided to the Fourier transform analyzer 314 by the way of the path 310 and paths 332 and 334. The two different input channels of the Fourier transform analyzer 314 and also of the oscilloscope 316 are indicated by the Ch1 and Ch2 notations in FIG. 3.

The FIG. 3 instruments include a gain and phase analyzer 312 which may be of the type manufactured by Hewlett-Packard Corporation under the identification of model HP/4194A and a dual channel Fourier transform analyzer, 314 which may be a model 2032 analyzer manufactured by Bruel and Kjaer Instruments Incorporated of Marlborough, Mass. For convenience in viewing the signals being processed and indeed for generating a record of the type shown in FIGS. 5 and 6 herein, the processed information, information on the path 310 and paths 330 and 336, may be viewed with an oscilloscope as is indicated at 316 in FIG. 3. An oscilloscope, such as the Tektronix Corporation model 475, may be employed for this purpose. The excitation signal information shown in the upper waveform of each view in FIGS. 5 and 6 is provided to the oscilloscope 316 by way of the path 330 connecting with the energizing pulse generator 320. For permanent storage of the information flowing along the paths 330 and 336 and path 310 and to enable additional analyses of this information, a microprocessor data acquisition system indicated at 318 may be used. A Zenith Data Systems Corporation model Z-248 microcomputer equipped with an IEEE-488 interface module, model 01000-60300, as manufactured by Capital Equipment Corporation of Burlington, Mass., may be used as the computer 318. The computer 318 is especially desirable for the purpose of storing input and output signals in both the time-and-frequency-domains, as well as calculating the normalized difference Fourier transform spectra in the FIG. 3 apparatus. The gain phase analyzer 312 in FIG. 3 is used to periodically check and initially establish the gain of the transistor (304) as is established via the two biases (306) and (308).

The direct current conductivity information for the thin film detector cell, that is, the information shown in FIG. 4 of the drawings herein is obtained in the FIG. 3 apparatus by way of the electrometer instrument shown at 328. As is indicated by the arrows 324 and 326, a temporary connection of the electrometer instrument 328 to the thin film detector cell is contemplated since the input characteristics of an electrometer instrument are incompatible with the pulse excitation signal used in the processing of challenge gas information.

Figure 9:
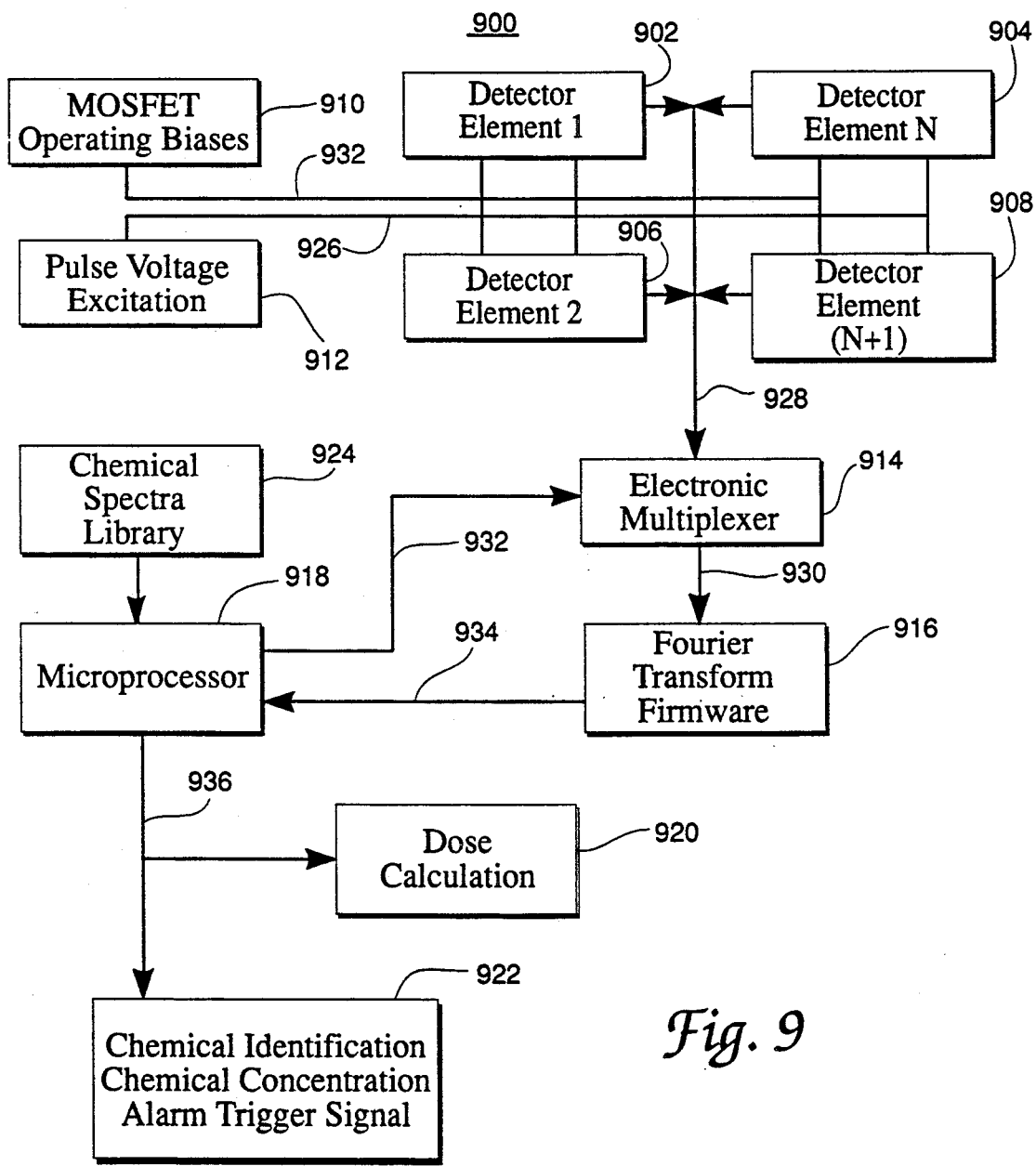
FIG. 9 shows a multiple detector element modification of the FIG. 3 system.

FIG. 9 of the drawings shows a system of the FIG. 3 type which also includes additional components useful in the actual identification of unknown components in a challenge gas, and in the determination of concentrations of the challenge gas unknown component. New to the signal processing apparatus in FIG. 9 is the array of detector elements 900, the electronic multiplexer circuit 914, the apparatus for dose calculation of block 920, and the apparatus for performing challenge gas identification concentration and alarm triggering of block 932. The FIG. 9 apparatus also includes a spectra library or memory apparatus in the block 924 and a plurality of identified signal communication paths.

During operation of the FIG. 9 apparatus, each of the detector elements 902, 904, 906, and 908 are provided with a different type of a chemically-active film of the metal-doped phthalocyanine or other type in order that the electrical conductivity response of the overall array 900 be unique for each different challenge gas mixture and concentration. As indicated by the "N" legend in the detector blocks 904 and 908, the number of detecting elements is not limited to the illustrated four elements, but may also include a larger array as will enable the generation of unique responses for a larger number of challenge gas mixtures and concentrations.

Operating bias for the amplifying transistors of the detector elements in the array 900 is established by the apparatus of block 910 in the manner shown in FIG. 1 herein. The operating bias signals are communicated to the detector element blocks by way of the path 932 while the excitation pulse signal for the N-detector element chemiresistor interdigitated arrays is provided by the block 912 and the path 926. Signals from the pulse excitation source and the detector elements in the array 900 are communicated by way of the multiconductor path 928 to the electronic multiplexer circuit 914 where the signals from the pulse excitation source and the individual detector elements are connected in controlled sequence and time duration to a single output path, 930, for input to the Fourier transform apparatus of block 916. The Fourier transform apparatus, as identified for the block 314 in FIG. 3, may be used at 916 in FIG. 9, or alternately, this function may be embodied in the form of software that is resident in a different type of firmware system such as a computer as is known in the electronic signal processing art.

Control of the electronic multiplexer circuit 914 may be accomplished by a microprocessor circuit as shown in block 918 by way of the control signal path 932. The data representing the Fourier transformation of the excitation pulse and the individual signals from the detector elements of the array 900 may be communicated to this microprocessor 918 along the path 934 in order that the storage of the transformed signals and comparison of the transformed signal waveforms with a memory resident library of chemical spectra transform waveforms represented in the block 924 is possible. The microprocessor calculates the normalized difference Fourier transform response and then tries to match this response with those results stored in the library of responses.

Comparisons are made in the microprocessor 918 between the calculated normalized difference Fourier transform waveforms received on the path 934 and the normalized difference Fourier transform waveform spectra data of the memory library 924. Best fit identifications of the unknown gas in the challenge mixture, and additionally, the concentration of the gas components in the challenge gas mixture can be achieved as is indicated by the block 922. A combination of quantity, type identity, and duration of presence of the unknown gas in the challenge gas mixture can be considered in generating the alarm trigger signal indicated in the block 922. Dose calculation, as indicated in the block 920, may also be performed in the microprocessor 918 by way of longer term consideration of both identity and time presence of a particular gas component in the challenge gas mixture.

In the FIG. 9 apparatus, it is desirable to first calculate the normalized difference Fourier transform and obtain a result before the processed data is compared with the spectra stored in the library.

The herein disclosed sensor requires supporting electronic circuitry that is, of course, more complicated than in the conventional direct current or single-frequency alternating current impedance based gaseous component detecting apparatus. The required circuitry is, however, currently available in discrete integrated circuit form and can be readily integrated into a small and unified design. For example, by fabricating the sensor of FIG. 1 using monolithic integrated circuit technology, a diffused resistor acting as a heat source and a diode acting as a temperature sensor could be utilized in combination to provide the stable 125° C. thermostated sensor environment desired herein. The FIG. 1 sensor therefore offers significant capabilities as an alternative technology for detecting a host of gaseous contaminants when coupled with an appropriate chemically-active film. The FIG. 1 sensor concept can be extended as shown in FIG. 9 to an array of discrete detector elements, with each detector element supporting a different chemically-active film, to be responsive to one or more different gaseous species. A microprocessor using known addressing and computational software may be employed at 918 to control the multiplexing of sensor signals and for processing the discrete responses of the sensors.

The microprocessor 918 in FIG. 9 may also be used in implementing pattern recognition software that is capable of performing the classical pattern recognition and identification calculations using the normalized difference Fourier transform spectra that are calculated from the signals received on the path 930 by using the library of comparison normalized difference Fourier transform spectra received from the block 924. An algorithm suitable for use in performing this block 918 pattern recognition and identification function is, for example, disclosed in my masters level academic thesis submitted to the U.S. Air Force Institute of Technology, Electrical and Computer Engineering Department at Wright-Patterson Air Force Base, Dayton, Ohio, under the title of "Computer Identification of Phonemes in Continuous Speech" and also identified as AFIT-GE-EE-78-D-20 dated December 1978. This Thesis is also available from the National Technical Information Service (NTIS) and the Defense Technical Information Center (DTIC) under the number AD-A064058.

This thesis includes source code listings, in the Fortran language, which were originally used for pattern identifications in the speech recognition art, but which are nevertheless, useful in other identification applications including the present Fourier transform gaseous component detection and identification function. The thesis discloses routines which enable the creation of a library of frequency-domain spectral data from calibration standards of selected time-domain signals. The thesis also illustrates use of this library via a cross-correlation pattern recognition algorithm to search a given time-domain signal that has been Fourier transformed in order to determine if any of the stored library elements are contained in the given signal. A percent of confidence detection factor is generated in the ensuing calculations. The program subroutines identified as follows are disclosed in this thesis document as separate routines that execute in an ordered sequence with the output of one routine serving as the input for a subsequently executing routine in accomplishing this cross-correlation pattern recognition calculation:

| 1. OCTAVE 1 | 3. PUNCH | 5. CRSCOR | 7. DECIS |
|---|---|---|---|
| 2. OCTAVE 2 | 4. PROAVE | 6. FPLOT | |

The contents of this academic thesis, including the Fortran routines, are hereby incorporated by reference into the present document.

The Fourier transform of the chemically-induced impedance response of the thin film sensing elements and the resulting unique envelopes of the normalized difference Fourier transform spectra are therefore herein shown to generate usable distinguishing "fingerprints". This normalized Fourier transformed difference response is also shown to be indicative of challenge gas concentrations. Additional specificity of the accomplished identification is also possible with a microprocessor controlled multiplexed array of discrete detector elements.

I claim:

1. A method for sensing the presence of selected compound components in a challenge gas effluent comprising the steps of:

exciting a thin film, chemical reaction modulated, electrical conductivity sensor with pulsed waveform electrical energy;

computing the normalized transform spectra frequency-domain envelope of said pulse waveform electrical energy;

exposing said sensor to said challenge gas effluent;

measuring the time-domain change in pulse excited electrical conductivity of said thin film sensor in response to said challenge gas effluent exposure;

determining the normalized transform spectrum frequency-domain envelope of said sensor time-domain electrical conductivity change;

subtracting said electrical conductivity change normalized transform spectrum envelope from said pulsed electrical excitation normalized transform spectrum envelope to obtain a fingerprint difference transform spectrum envelope representative of said challenge gas;

comparing said fingerprint difference transform spectrum envelope with the normalized difference spectrum envelope entries in a spectra file collection of selected gaseous compounds and concentrations;

identifying the incidents of predetermined matching degree between said challenge gas fingerprint normalized difference spectrum envelope and entries in said file collection of normalized difference transform spectra to confirm the presence of said selected gaseous compound components and concentrations in said challenge gas effluent.

2. The method of claim 1 wherein said sensor includes a metal-doped phthalocyanine thin film reactive membrane of predetermined thickness and wherein said method is preceded by the preliminary steps of:

purging said membrane with a predetermined non-reactive gas for an initial predetermined time interval and at a predetermined fixed temperature;

exposing said membrane to a predetermined concentration of said challenge gas at said predetermined fixed temperature and for a second predetermined time interval;

repeating said purging and exposing sequence a predetermined number of times.

3. The method of claim 1 further including the step of inducing in said sensor cell a reference thermodynamic equilibrium state prior to said challenge gas exposing step.

4. The method of claim 3 wherein said step of inducing in said sensor cell a reference thermodynamic state includes the isothermal temperature steps of:

exposing said sensor cell to a predetermined concentration of the selected compound component to be sensed for a first predetermined time interval;

purging said sensor cell by an exposure to clean inert gas for a second predetermined time interval;

repeating said exposing and purging steps in sequence for a predetermined number of times.

5. The method of claim 4 further including the step of:

reacting a fixed volume of said challenge gas effluent with said sensor cell for a predetermined time interval.

6. The method of claim 5 wherein:

said predetermined time intervals in said exposing, purging and reacting steps are each thirty minutes in length;

said predetermined concentration exposures include concentrations of twenty five parts-per-billion;

said clean inert gas in filtered ambient air;

said repeating step consists of three cycles of said exposing and purging; and said isothermal temperature is between one hundred and one hundred fifty degrees centigrade.

7. A method for analyzing a flow of unknown gas for the presence of constituent components comprising the steps of:

energizing a polymeric material gas component reactive detecting cell thin film element with a flow of electrical current which includes a waveform having a fundamental frequency and harmonics of said fundamental frequency;

exposing the detecting cell film to said stream of unknown gas;

comparing the time domain to frequency domain mathematical transform of the time responsive film electrical resistance determined detecting cell output signal with a known collection of such signals to identify components in said unknown gas.

8. The method of claim 7 wherein said mathematical transform is the Fourier transform.

9. The method of claim 8 wherein said electrical current signal is undulating in nature.

10. The method of claim 9 wherein said electrical current signal is pulsed in nature.

11. The method of claim 10 wherein said electrical current signal includes an impulse function waveform.

12. The method of claim 7 wherein said energizing and exposing steps include a plurality of different polymeric film material detecting cells and wherein said comparing step includes contrasting the electrical resistance output signal of said plurality of detecting cells with a plural cell collection of such signals to identify said unknown gas.

13. The method of claim 7 wherein said energizing, exposing, and comparing steps each include a plurality of different polymeric material detecting cells.

14. The method of claim 7 wherein said energized thin film is comprised of copper phthalocyanine.

15. The method of claim 7 further including the preliminary step of exposing said detecting cell thin film element to a predetermined concentration level of said predetermined constituent gases.

16. The method of claim 15 further including an alternating sequence of said preliminary step exposures and purging exposures.

* * * * *

UNITED STATES PATENT AND TRADEMARK OFFICE
CERTIFICATE OF CORRECTION

PATENT NO. : 5,071,770

DATED : December 10, 1991

INVENTOR(S) : Edward S. Kolesar

It is certified that error appears in the above-identified patent and that said Letters Patent is hereby corrected as shown below:

On the title page:
IN THE TITLE, "#3" should be deleted.
Col 1, line 02, "#3" should be deleted.
Col 4, line 50, "plurality of" should be deleted.
Col 4, line 51, "responses" should read --response--.
Col 4, line 53, "plurality of" should be deleted.

Col 5, line 29, the symbol preceding "-electron" should be --Π--.
Col 8, line 28, "gm" should read --$g_m$--.
Col 10, line 35, "Celcius" should read --Celsius--.
Col 13, line 62, "concentration" should read --concentrations--.
Col 15, line 03, a hyphen should follow "peak".

Signed and Sealed this

First Day of June, 1993

*Attest:*

MICHAEL K. KIRK

*Attesting Officer*   Acting Commissioner of Patents and Trademarks